United States Statutory Invention Registration [19]

[11] Reg. Number: H839

Carlon [43] Published: Nov. 6, 1990

[54] FABRIC MOISTURE DETECTOR

[75] Inventor: Hugh R. Carlon, Fallston, Md.

[73] Assignee: The United States of America as represented by the Secretary of the Army, Washington, D.C.

[21] Appl. No.: 432,823

[22] Filed: Nov. 7, 1989

[51] Int. Cl.[5] ..... G01R 27/02

[52] U.S. Cl. ..... 324/694

*Primary Examiner*—Thomas H. Tarcza
*Assistant Examiner*—Linda J. Wallace
*Attorney, Agent, or Firm*—Anthony T. Lane; Edward Goldberg; Michael C. Sachs

[57] ABSTRACT

A fabric moisture detector and method is provided. The detector has a support insulating structure, and a pair of electrodes, which have a pair of opposite faces separated by a gap of selective thickness, such as four inches or ten centimeters. The detector also has a current sensor, for measuring the current through the gap during the application of a relatively high voltage, such as about 10,000 volts to 60,000 volts for a ten centimeter gap. The voltage applied using a ten centimeter gap can be between about 1,000 volts per gap centimeter to 6,000 volts per gap centimeter. The process includes the steps of measuring the gap current during the application of the specified voltage, whereby a dry fabric or bare electrodes yields substantially no current and a wet fabric yields a peak current.

12 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FABRIC MOISTURE DETECTOR

GOVERNMENTAL INTEREST

The invention described herein may be made, used or licensed by the Government for governmental purposes without the payment of any royalties thereon or therefor.

The invention relates to a fabric moisture detector, and in particular the invention relates to a fabric moisture detector having a pair of high voltage electrodes.

BACKGROUND OF THE INVENTION

The prior art fabric moisture detector included an evaporator and a condenser.

One problem with the prior art fabric moisture detector is the relatively slow operation of the detector.

It is believed that there ia unpublished test data which shows accelerated drying of fabric wetted with water, when subject to an electric potential of about 10,000 volts.

SUMMARY OF THE INVENTION

According to the present invention, a fabric moisture detector is provided. This detector comprises a support structure; a pair of electrodes having a space therebetween and having respective conductors; and a heating coil subassembly having a pair of connecting wires: whereby a fabric specimen which is disposed in the space between the pair of spared electrodes is tested for moisture.

By using the pair of spaced electrodes for testing a fabric specimen disposed therebetween, current, which indicates the moisture, is measured by a current meter during the application of a high voltage through the electrodes.

The foregoing and other objects, features and advantages will be apparent from the following description of the preferred embodiment of the invention as illustrated in the accompanying drawings.

DESCRIPTION OF THE PREFERRED EMBODIMENT

Figure 1:
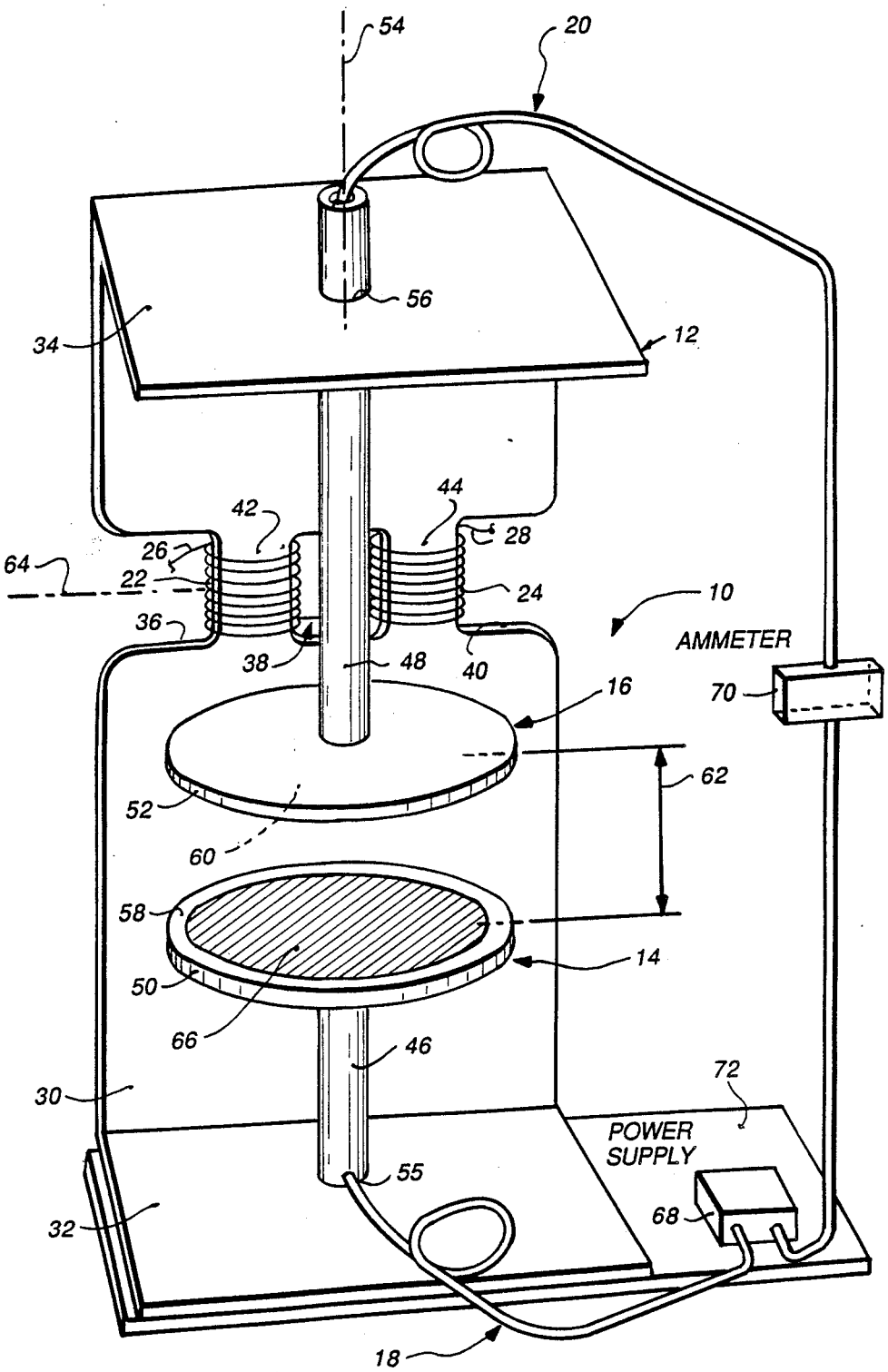
FIG. 1 is a perspective view of a fabric moisture detector according to the invention.

As shown in FIG. 1, a moisture or vapor detector or assembly 10 is provided. Assembly 10 has a support insulating structure 12, and a pair of spaced lower and upper electrodes 14, 16, which have respective lower and upper conductors 18, 20. Assembly 10 also has a pair of left and right heater coils 22, 24, which have respective wires 26, 28. Coils 22, 24 heat the parts of the support structure 12 on which they are wrapped for preventing condensation and a short circuit around electrodes 14, 16.

Support 12 has a vertical wall 30, and a lower horizontal wall 32, which ia fixedly connected to vertical wall 30, and an upper horizontal wall 34, which is fixedly connected to vertical wall 30.

vertical wall 30, has three cutouts 36, 38, 40, which form two vertical coil posts 42, 44, on which respective heater coils 22, 24 are wound.

Lower and upper electrodes 14, 16 have respective lower and upper solid rods 46, 48, and respective lower and upper disks 50, 52, which are fixedly connected to respective rods 46, 48. Rods 46, 48 and disks 50, 52 have a common centerline 54.

Lower rod 46 is fixedly connected at its lower end 55 to lower horizontal wall. Upper rod 48 extends through a hole 56 in upper horizontal wall 34. Upper rod 48 is press fit into hole 56, to provide vertical movement, when an axial force is applied to rod 48, of rod 48 relative to wall 34. Disks 50, 52 have respective faces 58, 60, which are separated by a gap 62. The size of gap 62 is set by moving upper disk 52 relative to lower disk 50.

Heater coils 22, 24 are arranged symmetrically about a horizontal axis 64. Disk face 58 supports a substrate or sample or specimen 66, which is shown in FIG. 1 in position for a test.

Electrode conductors 18, 20 are connected in series to a voltage source or supply 68, and through a current meter 70 for sensing current. Source 68 and assembly 10 rest on a table top 72.

Materials and sizes of parts of assembly 10 are indicated hereafter. Rods 46, 48 are composed of stainless steel. Disks 50, 52 are composed of stainless steel. Support 12 is composed of a polystyrene material, which is an electrical insulation material. Gap 62, which is adjustable, has a range of about up to 10 centimeters.

Figure 2:
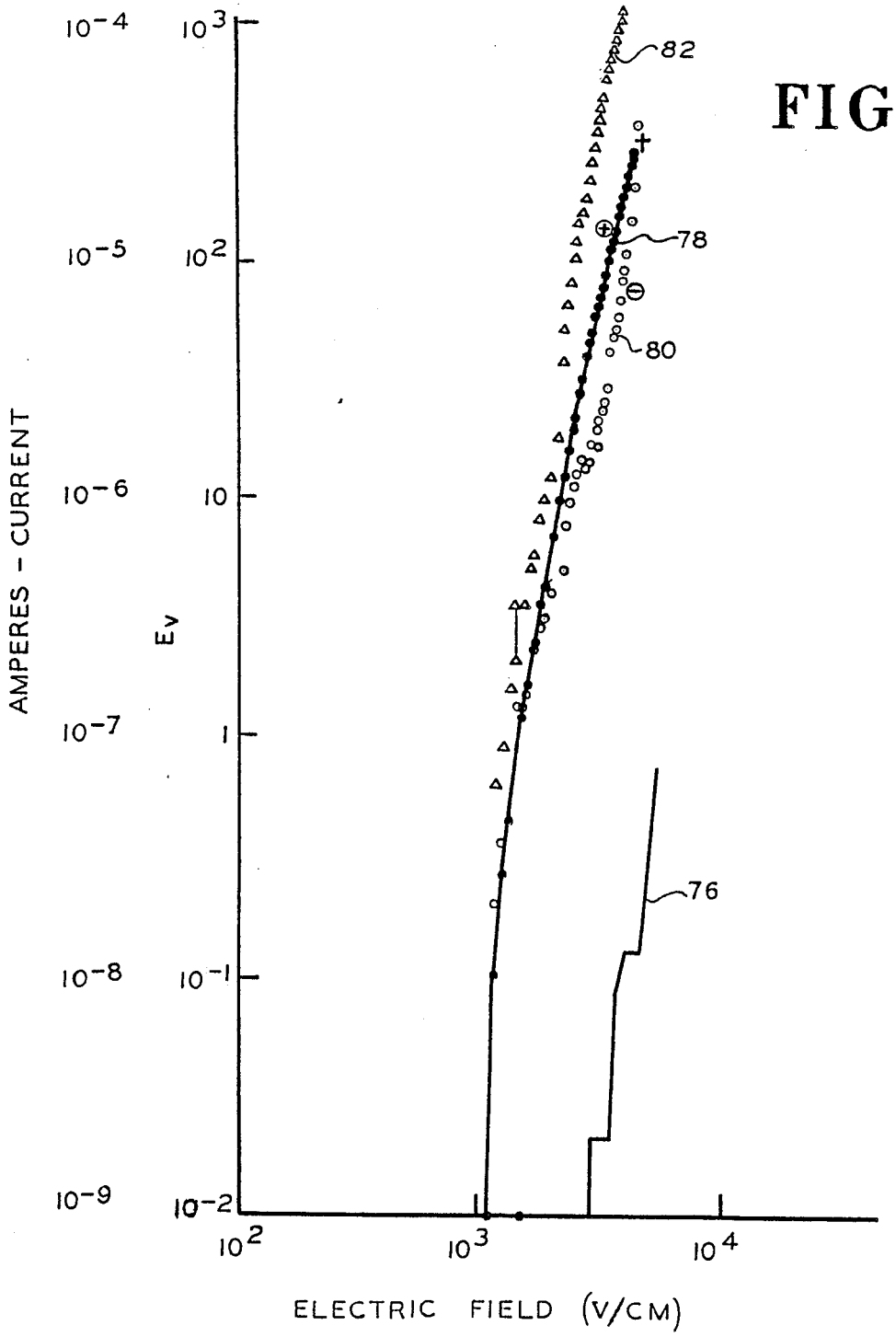
FIG. 2 is a graph for linen wet with water showing electric field along the x-axis (v/cm.) versus current (amperes) and $E_V$ along the y-axis.
Figure 3:
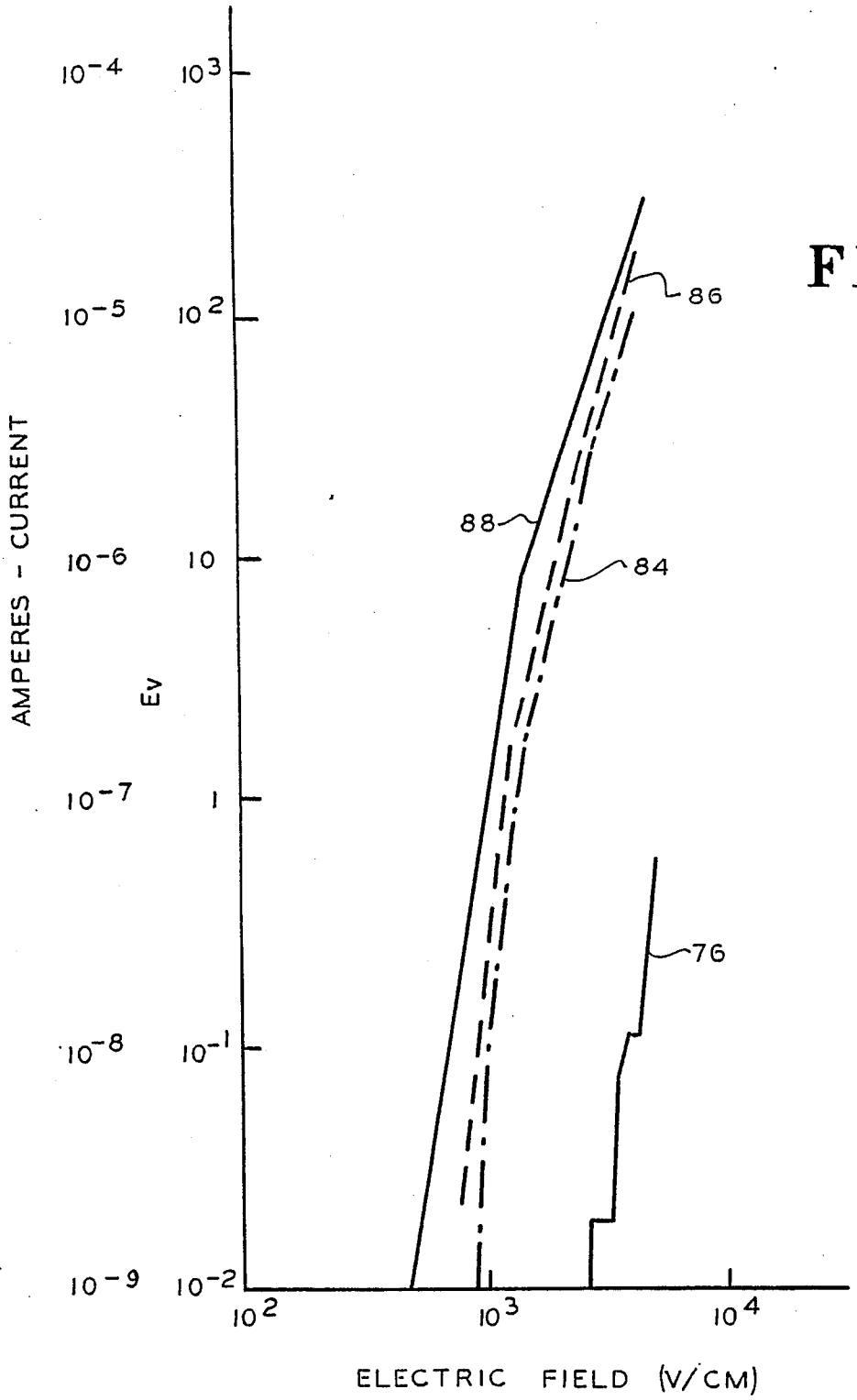
FIG. 3 is a graph for linen wet with liquid showing electric field along the x-axis (v/cm. versus current (amperes) and $E_V$ along the y-axis.

As shown in FIGS. 2 and 3, a number of test curves of water and other liquids are shown. The curves include:

a dry electrode (B) curve 76 in FIGS. 2 and 3; and
a wet positive electrode water (C) curve 78,
a wet negative electrode water (D) curve 80,
both wet electrodes water (E) curve 82 in FIG. 2; and
a lower light oil (F) curve 84,
a middle turpentine (G) curve 86, and
an upper 75% ethanol, water and over 50% acetone mixture (H) curve 88 in FIG. 3.

It is noted that curves 80 and 82 each has only the curve points shown, without the curve line, for ease of illustration.

A linen fabric, and a gap of 10 centimeters, was preferably used in the tests for the data of FIGS. 2 and 3. A cotton fabric was also used. The tests covered various liquids in respective substrates, including water of curves 78, 80, 82, in FIG. 2, and light oil of curve 84, turpentine of curve 86, and a mixture of 75% ethanol, water and over 50% acetone of curve 88 in FIG. 3. The tests also covered a non-liquid, dry condition in curve 76. The tests using water in the substrate included three tests, including a first test with the water in the substrate, on the positive electrode of curve 78, a second test with the water in the substrate on the negative electrode of curve 80, and a third test with the water in substrates on both the positive and negative electrodes of curve 82.

In summary, the invention relates to a method and apparatus for detecting with relative great sensitivity even slight amounts of moisture in a fabric 66, or other porous material, by using an electric field. A very sharp increase in current occurs in an electric field greater than about 1,000 volts per centimeter (v/cm.), when relatively slight moisture is present in the substrate or sample 66, compared to the current when the substrate is dry. If substrates are placed on both electrodes, the current is greater than for either electrode alone.

The electrode disks 50, 52 are disposed parallel to each other. Support 12 is an insulator. Current, which passes between disks, 50, 52, passes through a vapor from the liquid of the substrate 66. Such current can be measured with relatively great accuracy by meter 70, which is a conventional current meter. Coils 22, 24, are conventional heater wire coils, which are wound on respective posts 42, 44 of insulating structure 12.

In FIGS. 2 and 3, test results are shown. In (B) curve 76, results for a perfectly dry cloth substrate show little or no current on the ampere scale and the E$\nu$ scale. In (C), (D) and (E) curves 78, 80, 82, slight dampness produced a sharp rise in current. Such dampness or wetness can produce a current of up to 100,000 times the current measured for dryness or slight dampness.

It is noted that if a damp fabric is placed on the lower disk and a paddle which is composed of polystyrene insulating material and which is passed between the disks 50, 52, the ions or charge carriers produced from the damp fabric are blocked and cannot reach the opposite disk 52, whereby the current drops to near zero.

In FIG. 3, in (F) curve 84, test results for light oil are shown. In (G) curve 86, test results for turpentine are shown. In (H) curve 88, test results for a mixture of 75 percent strength ethanol plus water plus over 50 percent strength acetone are shown.

Besides linen fabric, other materials for the substrate 66 work well, including wet cotton, wet paper napkin, wet toweling, wet sheet sponge, wet nylon pad and wet nylon webbing. Wetted wire screening also works well. Fine layers of water condensation which is placed on the electrode disks 50, 52 also works well.

Liquid water alone, when placed on the bare electrode disk 50, without a fabric or like substrate, does not work; and gives a test result of about zero current.

Some volatile liquids, including acetone and ethanol, give a small current, when placed on the bare electrode disk 50.

The advantages of assembly 10 and its related method are indicated hereafter.

(A) Assembly 10 can operate relatively fast for testing samples.

(B) Assembly 10 avoids the prior art problem of slow operation in testing samples.

(C) Assembly 10 can test for dampness in many types of fabrics and many types of porous materials.

(D) Assembly 10 can test for dampness due to many types of liquids in fabrics including organic liquids and inorganic liquids.

While the invention has been described in its preferred embodiment, it is to be understood that the words which have been used are words of description rather than limitation and that changes may be made within the purview of the appended claims without departing from the true scope and spirit of the invention in its broader aspects.

The embodiments of an invention in which an exclusive property or right is claimed are defined as follows:

1. A fabric wetness detector comprising:

a support structure;

a pair of spaced electrodes having opposite faces separated by a gap of selective dimension for receiving therebetween a fabric portion to be tested; and a current sensor connected to the pair of electrodes for measuring a current passing through the gap and fabric portion during an application of a voltage from a power supply above approximately 1,000 volts per gap centimeter to the electrodes.

2. The detector of claim 1, wherein the gap is at least a fraction of a centimeter in thickness.

3. The detector of claim 1, wherein the fabric is a material like linen or cotton, and the fabric dampness to be tested is water moisture in the fabric, and the gap thickness is about 10 centimeters.

4. The detector of claim 1, wherein the support structure includes a lower horizontal wall, a vertical wall supported by the lower horizontal wall, and an upper horizontal wall supported by the vertical wall.

5. The detector of claim 4, wherein the support structure is composed of a polystyrene insulating material.

6. The detector of claim 4, wherein the vertical wall has at least three cutouts forming at least two posts for supporting heater coils.

7. The detector of claim 1, wherein the pair of spaced electrodes include a lower rod, an upper rod, a lower disk fixedly connected to the lower rod, and an upper disk fixedly connected to the upper rod, and wherein the disks have the electrode faces.

8. The detector of claim 7, wherein the lower rod and disk and upper rod and disk are coaxial along a common vertical centerline, and wherein the lower rod is fixedly connected to the support structure, and the upper rod and disk are adjustable relative to the lower rod and disk for adjusting the thickness of the gap.

9. The detector of claim 1, wherein the current sensor includes a voltage source having a pair of connectors connected in series to the pair of electrodes, and through a current meter.

10. The detector of claim 6, including heater means having a pair of vertical heater coils, said coils being wound respectively on said posts, for heating the posts and vertical wall in order to prevent wall condensation for preventing a short circuit around the electrodes.

11. A process for sensing moisture in a porous material including the steps of:

placing the porous material to be tested between a pair of high voltage electrodes separated by a gap having a thickness of about ten centimeters;

applying a voltage potential across the pair of electrodes, said potential being between 10,000 volts to 60,000 volts; and measuring the current passing through the gap between the electrodes during the application of voltage, whereby a relatively high current indicates moisture in the porous material.

12. A process of detecting wetness in a porous material due to a liquid in the porous material, including the steps of;

placing the porous material with the wetness between a pair of high voltage electrodes separated by a gap having a thickness of selective number of centimeters;

applying a voltage potential across the pair of electrodes, said potential being between 1,000 volts per centimeter of gap thickness to 6,000 volts per centimeter of gap thickness; and measuring the current passing through the gap between the electrodes during the application of the voltage, whereby a relatively high current during voltage application indicates wetness in the porous material.

* * * * *